United States Patent
Masin et al.

(10) Patent No.: US 9,662,051 B2
(45) Date of Patent: May 30, 2017

(54) AUTOMATED ASSESSMENT OF PERIPHERAL VASCULAR CONDITION

(71) Applicant: D. E. Hokanson, Inc., Bellevue, WA (US)

(72) Inventors: Donald I. Masin, Bellevue, WA (US); Molly Ciliberti, Sammamish, WA (US); Kyra M. Gray, Redmond, WA (US)

(73) Assignee: D.E. Hokanson, Inc., Bellevue, WA (US)

( * ) Notice: Subject to any disclaimer, the term of this patent is extended or adjusted under 35 U.S.C. 154(b) by 458 days.

(21) Appl. No.: 13/791,806

(22) Filed: Mar. 8, 2013

(65) Prior Publication Data

US 2014/0257062 A1    Sep. 11, 2014

(51) Int. Cl.

| A61B 5/02 | (2006.01) |
|---|---|
| A61B 5/1455 | (2006.01) |
| A61B 5/022 | (2006.01) |
| A61B 5/021 | (2006.01) |
| A61B 5/026 | (2006.01) |

(52) U.S. Cl.
CPC .......... *A61B 5/14551* (2013.01); *A61B 5/022* (2013.01); *A61B 5/0261* (2013.01); *A61B 5/02141* (2013.01); *A61B 5/14552* (2013.01)

(58) Field of Classification Search
CPC ... A61B 5/0049; A61B 5/0059; A61B 5/0261; A61B 5/14542; A61B 5/14551
See application file for complete search history.

(56) References Cited

U.S. PATENT DOCUMENTS 5,050,613 A * 9/1991 Newman ............ A61B 5/02007
                                                            600/483
5,766,127 A * 6/1998 Pologe ................. A61B 5/0261
                                                            600/310

(Continued)

FOREIGN PATENT DOCUMENTS

| EP | 1 861 000 A | 12/2007 |
|---|---|---|
| WO | 2006/097866 A1 | 9/2006 |

OTHER PUBLICATIONS

Al-Qaisi, M et al. Ankle Brachial Pressure Index (ABPI): An update for practitioners. Vascular Health and Risk Management. vol. 5, p. 833-841, 2009.*

(Continued)

*Primary Examiner* — Catherine B Kuhlman
(74) *Attorney, Agent, or Firm* — Christensen O'Connor Johnson Kindness PLLC (57) ABSTRACT

An automated assessment of a patient's peripheral vascular condition includes using a pulse oximeter to generate at least a perfusion index relative to a limb or digit of the patient. Pressure is applied to the limb or digit, and while increasing or decreasing the pressure, a change in the perfusion index is determined. The change is indicative of a cessation of blood flow or a return of blood flow in the limb or digit. A systolic blood pressure is thereafter determined based on the pressure applied at the time of cessation of blood flow or the return of blood flow in the limb or digit. Using a pulse oximeter to generate a perfusion index may include transmitting light into the limb or digit, detecting light that was transmitted into tissue in the limb or digit, and calculating the perfusion index based on the light transmitted through the tissue.

19 Claims, 5 Drawing Sheets

(56) References Cited

U.S. PATENT DOCUMENTS

| | | | |
|---|---|---|---|
| 6,322,515 B1 | 11/2001 | Goor | |
| 6,909,912 B2 | 6/2005 | Melker | |
| 7,247,142 B1 | 7/2007 | Elmandjra | |
| 7,553,285 B2 | 6/2009 | Mao | |
| 7,569,017 B2 | 8/2009 | Mao | |
| 7,582,060 B2 | 9/2009 | Mao | |
| 8,417,307 B2* | 4/2013 | Presura | A61B 5/14551 600/324 |
| 9,326,711 B2* | 5/2016 | Kracker | A61B 5/14542 |
| 2002/0082488 A1* | 6/2002 | Al-Ali | A61B 5/14551 600/323 |
| 2006/0074283 A1* | 4/2006 | Henderson et al. | 600/315 |
| 2010/0081892 A1 | 4/2010 | Sethi | |
| 2010/0292586 A1 | 11/2010 | Rooke | |

OTHER PUBLICATIONS

Bianchi, J et al. Pulse oximetry index: a simple arterial assessment for patients with venous disease. Journal of Wound Care. vol. 17 No. 6, p. 253-260, Jun. 2008.*

Lima, A.P., et al., "Use of a Peripheral Perfusion Index Derived From the Pulse Oximetry Signal as a Noninvasive Indicator of Perfusion," Critical Care Medicine 30(6):1210-1213, Jun. 2002.

International Search Report and Written Opinion mailed May 30, 2014, in International Patent Application No. PCT/US2014/020844, filed Mar. 5, 2014, 9 pages.

Alnaeb, M.E, et al., "Prospective Assessment of Lower-Extremity Peripheral Arterial Disease in Diabetic Patients Using a Novel Automated Optical Device," Angiology 58(5):579-585, Oct.-Nov. 2007.

Bianchi, J., "LOI: An Alternative to Doppler in Leg Ulcer Patients," Wounds UK 1(1):80, 82-85, May 2005.

Bianchi, J., et al., "Pulse Oximetry: A New Tool to Assess Patients With Leg Ulcers," Journal of Wound Care 9(3):109-112, Mar. 2000.

Bianchi, J., et al., "Pulse Oximetry Index: A Simple Arterial Assessment for Patients With Venous Disease," Journal of Wound Care 17(6):253-258, 260, Jun. 2008.

Blanchfield, D., "Introduction of the Lanarkshire Oximetry Index in Community Nursing," Wound Practice and Research 16(2):30, 32-34, 36, 37, May 2008.

Couse, N.F., et al., "Pulse Oximetry in the Diagnosis of Non-Critical Peripheral Vascular Insufficiency," Journal of the Royal Society of Medicine 87(9):511-512, Sep. 1994.

Ignjatović, N., et al., "Diagnostic Importance of Pulse Oximetry in the Determination of the Stage of Chronic Arterial Insufficiency of Lower Extremities," Srpski Arhiv Za Celokupno Lekarstvo 138(5-6):300-304, May-Jun. 2010.

Ingram, G., and N. Munro, "The Use (or Otherwise) of Pulse in General Practice," British Journal of General Practice 55(516):501-502, Jul. 2005.

Joyce, W.P., et al., "Pulse Oximetry: A New Non-Invasive Assessment of Peripheral Arterial Occlusive Disease," British Journal of Surgery 77(10):1115-1117, Oct. 1990.

Kwon, J.N., and W.B. Lee, "Utility of Digital Pulse Oximetry in the Screening of Lower Extremity Arterial Disease," Journal of the Korean Surgical Society 82(2):94-100, Feb. 2012.

Papanas, N., et al., "Lanarkshire Oximetry Index as a Diagnostic Tool for Peripheral Arterial Disease in Type 2 Diabetes: A Pilot Study," Angiology 61(4):388-391, May 2010.

Parameswaran, G.I., et al., "Pulse Oximetry as a Potential Screening Tool for Lower Extremity Arterial Disease in Asymptomatic Patients With Diabetes Mellitus," Archives of Internal Medicine 165(4):442-446, Feb. 2005.

Sardina, D., "Lanarkshire Oximetry Index," Wound Care Advisor, 2 pages, at least as early as Sep. 16, 2014.

Talke, P., et al., "Does Measurement of Systolic Blood Pressure With a Pulse Oximeter Correlate With Conventional Methods?" Journal of Clinical Monitoring 6:(1):5-9, Jan. 1990.

Vowden, K., and P. Vowden, "Doppler and ABPI or LOI in Screening for Arterial Disease," Wounds UK 2(1):13-16, Mar. 2006.

Wu, S.C., et al., "Foot Ulcers in the Diabetic Patient, Prevention and Treatment," Vascular Health and Risk Management 3(1):65-76, Feb. 2007.

Davies, J.H., et al., "Current Utility of the Ankle-Brachial Index (ABI) in General Practice: Implications for Its Use in Cardiovascular Disease Screening," BMC Family Practice 15(69), Apr. 2014, 11 pages.

\* cited by examiner

AUTOMATED ASSESSMENT OF PERIPHERAL VASCULAR CONDITION

TECHNICAL FIELD

The present application relates to an automated medical apparatus and methods for assessing a peripheral vascular condition of a patient.

BACKGROUND

Figure 1:
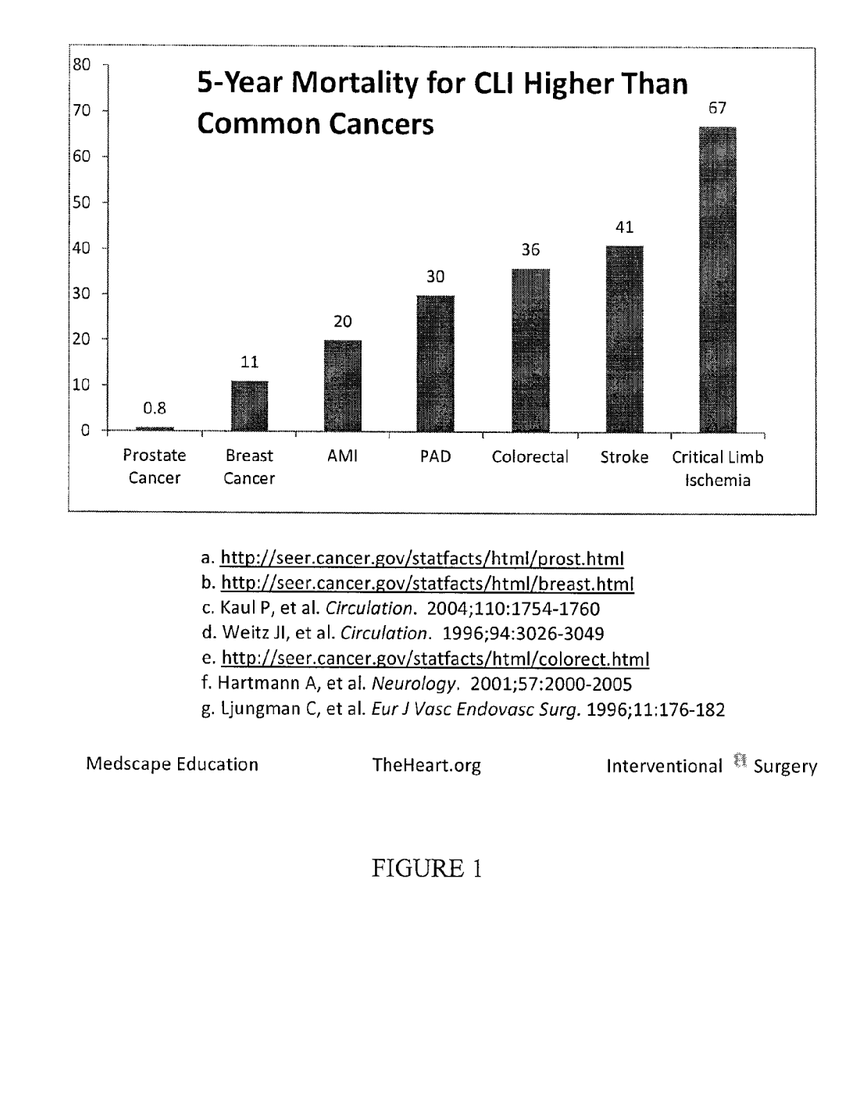
FIG. 1 is a graph showing the 5-year mortality of critical limb ischemia relative to common cancers.

Peripheral Arterial Disease (PAD) is an international epidemic of a significant size. For example, in the United States, an estimated 12-20 million people are affected. Closely related to diabetes mellitus, PAD is the peripheral vascular component of the systemic disease atherosclerosis which also causes heart attack and stroke. The incidence of PAD is increasing rapidly. Once PAD becomes critical limb ischemia, the 5-year mortality is worse than cancer, heart attack, and stroke, with 69% mortality as illustrated in FIG. 1. People with coronary heart disease and/or carotid disease who also have PAD have 3 to 6 times the risk of a coronary event or stroke as those without PAD.

PAD is called a multi-vessel disease when it is in the peripheral arteries of the legs, the carotid arteries of the neck, and/or the coronary arteries of the heart. Because 90% of people with PAD have no symptoms and are unaware that they have the disease, it often goes unnoticed until they have either a cardiac event or cerebrovascular accident (CVA), or if it progresses until there is critical limb ischemia with severe leg pain on exertion, which can lead to amputation. Due to the "invisibility" of PAD, it is difficult to accurately determine how many people have PAD.

The American Heart Association, the American College of Cardiology, the American Diabetes Association, the American College of Physicians, and others, have generated a series of PAD-related guidelines that were revised in January 2011. They believe it is imperative that primary care physicians perform screening for PAD, especially with diabetic patients. Because of the increasing incidence and lower age of people developing PAD, they also reduced the recommended screening age.

A typical patient who should be screened for PAD often presents with a cluster of diseases such as diabetes, hypertension, dyslipidemia, coronary artery disease (CAD), and CVA or stroke. Only about 10% of all patients with PAD are symptomatic.

The definitive screening exam for PAD is an Ankle Brachial Index or ABI, and for patients with calcified vessels in their legs, a Toe Brachial Index or TBI. These exams have traditionally been performed by vascular specialists and vascular surgeons using a continuous wave (CW), bi-directional (zero-crossing) Doppler. The ABI is a non-invasive test that compares the highest systolic brachial pressure of the two arms to the highest ankle pressure in each leg by dividing the ankle pressure by the brachial pressure. The resulting number is the Ankle Brachial Index. A person with two legs has two ABI readings. A normal ABI is 1.0. A number below 0.99 shows the presence of decreased arterial blood flow due to PAD, with the disease severity increasing as the index decreases. Occasionally a diabetic patient will have very stiff vessels that are incompressible due to calcification of the arterial walls, and he will have an ABI greater than 1.3. To determine perfusion to the foot, these patients should also have a TBI performed, since vessels of the toe do not normally calcify like those of the legs.

Presently, a CW, bi-directional Doppler is recognized as the appropriate instrument for performing ABI measurements. ABI measurements taken using a CW Doppler are reimbursable by the Centers for Medicare and Medicaid Services (CMS). In the United States, Doppler is currently recognized as the gold standard for performing the ABI.

It is important in clinical practice to measure blood pressures for the ABI or TBI using the same technology and technique on the patient so that the pressures obtained from multiple locations on the patient can be directly compared. Other techniques of measuring blood pressure in the brachial arteries are also used; however, they have been shown to be unreliable and inaccurate when applied to the ankle arteries.

Most primary care physicians, unlike the vascular specialists currently performing ABI exams, have little or no recent experience using a Doppler and may feel uncomfortable relying on their own expertise to perform, analyze, and diagnose disease using this instrument. They are wary of sending a false-positive patient to a vascular surgeon and experiencing the embarrassment when, upon ultrasound scanning performed by the vascular surgeon, the patient is told there is no disease. They are also wary of the reverse when a false-negative results in missing a diseased limb that needs follow-up.

Through experience, vascular clinicians are able to find the best location over an artery where a clean waveform can be achieved with excellent Doppler sound, and by inflating a vascular cuff, obtain an accurate systolic pressure measurement. This involves specialized technique, applying the right size cuff, holding the Doppler sensor at the correct angle in regard to the arterial walls and subsequent blood flow, recognizing what is heard, understanding how to inflate and deflate the cuff correctly, and finally calculating the index for each leg.

As mentioned above, ABI and TBI examinations are reimbursable in the United States provided the procedure meets CMS requirements. If a resultant ABI is abnormally high (>1.3), then toe pressures are substituted for the ankle pressures since, unlike the legs, the toes do not calcify and are compressible. The pressures in the toes are measured by putting a pressure cuff on the toe and obtaining a photoplethysmograph waveform (PPG) distally on the pad of that toe. The resultant TBI reflects an accurate state of the arteries in the patient's legs. PPG is the standard instrument used to determine toe pressures in the United States because it is more accurate and easier to use than a CW Doppler. It is most difficult to perform a toe pressure using a Doppler since there is no major artery near the surface of the pad on the bottom of the toe, whereas the PPG transducer can be attached to the pad of the toe with Velcro, a clip, or tape, and can detect blood flow via the pulsating arterioles.

As with Doppler, photoplethysmography is not commonly practiced in primary care physician offices, and as such, the clinicians are typically not familiar with normal waveforms and the associated readings.

Providing a physician or other medical clinician with an easy-to-use, accurate, and reliable means of performing an ABI and/or TBI, either singularly or in conjunction with a bi-directional Doppler, can provide reassurance that the results are accurate, especially when the actual measurements and calculations are performed automatically and are verifiable.

SUMMARY

Described herein is an automated method of assessing a peripheral vascular condition of a patient. In at least one embodiment, under control of a computing device, the method includes using a pulse oximeter to generate a perfusion index (PI) relative to a limb or digit of the patient. Pressure is applied to the limb or digit of the patient, and while increasing or decreasing the pressure, a change in the perfusion index relative to the limb or digit is determined. The change in the perfusion index is indicative of a cessation of blood flow or a return of blood flow in the limb or digit. A systolic blood pressure in the limb or digit is determined based on the pressure applied at the time of cessation of blood flow or the return of blood flow in the limb or digit. The resultant systolic pressure determinations are used to calculate ABI and TBI measurements.

In various embodiments, a pressure cuff is used to compress the limb or digit of the patient. The pressure cuff may inflate or deflate at a controlled rate.

In various embodiments, a pulse oximeter generates a perfusion index by transmitting light into the limb or digit, detecting light that was transmitted through tissue in the limb or digit, and calculating the perfusion index relative to the limb or digit based on the light transmitted through the tissue. Determining a change in the perfusion index indicative of a cessation of blood flow in the limb or digit may include identifying when a decrease in the perfusion index occurs. Alternatively (or additionally), a change in the perfusion index indicative of a return of blood flow in the limb or digit may be determined by identifying when an increase in the perfusion index occurs.

In various embodiments, an assessment index such as an ABI may be calculated by dividing a systolic blood pressure determined in an ankle of the patient by a systolic blood pressure determined in an arm of the patient. Alternatively (or additionally), an assessment index such as a TBI may be calculated by dividing a systolic blood pressure determined in a toe of the patient by a systolic blood pressure determined in an arm of the patient.

In various embodiments, while increasing or decreasing the pressure applied to the limb or digit, the above-described methods may further include monitoring a change in oxygen saturation ($SpO_2$) of the blood in the limb or digit indicative of a cessation of blood flow or a return of blood flow in the limb or digit. A systolic blood pressure in the limb or digit is determined based on the pressure applied when the cessation of blood flow or the return of blood flow occurred, as indicated by the change in the perfusion index and by the change in oxygen saturation.

In various embodiments, while increasing or decreasing the applied pressure, the above-described methods may include further monitoring a volumetric pulse waveform of the blood in the limb or digit for a change indicative of a cessation of blood flow or a return of blood flow in the limb or digit. A systolic blood pressure in the limb or digit is determined based on the pressure applied when the cessation of blood flow or the return of blood flow occurred, as indicated by the change in the perfusion index and by the change in the volumetric pulse waveform.

In various embodiments, while increasing or decreasing the applied pressure, the above-described methods may further include monitoring oxygen saturation and a volumetric pulse waveform of the blood in the limb or digit for a change indicative of a cessation of blood flow or a return of blood flow. A systolic blood pressure in the limb or digit is determined based on the pressure applied when the cessation of blood flow or the return of blood flow occurred, as indicated by the change in the perfusion index, the change in oxygen saturation, and the change in the volumetric pulse waveform.

Also described herein is an apparatus for assessing a peripheral vascular condition of a patient. In at least one embodiment, the apparatus may include a pressure cuff and a processor. The pressure cuff is configured to apply pressure to a limb or digit of the patient to cause cessation of blood flow in the limb or digit. The processor is configured to cause the pressure cuff to controllably apply or release pressure to the limb or digit of the patient. The processor is further configured to monitor a perfusion index calculated by a pulse oximeter relative to the limb or digit and determine a change in the perfusion index indicative of a cessation of blood flow or a return of blood flow in the limb or digit. The processor determines a systolic blood pressure in the limb or digit based on the pressure applied by the pressure cuff when the cessation of blood flow or the return of blood flow occurred.

In various embodiments, the pressure cuff is configured to apply pressure to the limb or digit by inflating and compressing the limb or digit. The processor may be configured to cause the pressure cuff to controllably apply or release pressure by inflating or deflating the pressure cuff at a controlled rate.

In various embodiments, the apparatus may include one or more optical devices configured to transmit and detect light when attached to the patient. The perfusion index is monitored using data generated by the pulse oximeter, the sensor of which includes one or more optical devices. The optical devices may be configured to transmit light into the limb or digit and detect light transmitted through tissue in the limb or digit, and the processor may be configured to monitor the perfusion index calculated by the pulse oximeter based on the light transmitted through the tissue.

In various embodiments, one or more optical devices may comprise an optical source configured to transmit light at specific wavelengths and a photodiode configured to detect light transmitted at the specific wavelengths. One or more optical devices may comprise a pulse oximeter sensor, and the processor may be configured to receive the perfusion index from the pulse oximeter.

In various embodiments, the processor may further be configured to calculate an assessment index such as an ABI by dividing a systolic blood pressure determined in an ankle of the patient by a systolic blood pressure determined in an arm of the patient.

Alternatively (or additionally), the processor may be configured to calculate an assessment index such as a TBI by dividing a systolic blood pressure determined in a toe of the patient by a systolic blood pressure determined in an arm of the patient.

In various embodiments, while causing the pressure cuff to controllably apply or release pressure to the limb or digit of the patient, the processor may be further configured to monitor oxygen saturation of the blood in the limb or digit for a change in oxygen saturation indicative of a cessation of blood flow or a return of blood flow in the limb or digit. A systolic blood pressure in the limb or digit is determined based on the pressure applied when the cessation of blood flow or the return of blood flow occurred as indicated by the change in the perfusion index and by the change in the oxygen saturation.

In various embodiments, while causing the pressure cuff to controllably apply or release pressure to the limb or digit of the patient, the processor may be further configured to monitor a volumetric pulse waveform of the blood in the limb or digit for a change indicative of a cessation of blood flow or a return of blood flow in the limb or digit. A systolic blood pressure in the limb or digit is determined based on the pressure applied when the cessation of blood flow or the return of blood flow occurred as indicated by the change in the perfusion index and by the change in the volumetric pulse waveform.

In various embodiments, while causing the pressure cuff to controllably apply or release pressure to the limb or digit of the patient, the processor may be further configured to monitor oxygen saturation and the volumetric pulse waveform of the blood in the limb or digit. A systolic blood pressure in the limb or digit is determined based on the pressure applied when the cessation of blood flow or the return of blood flow occurred as indicated by the change in the perfusion index, the change in the oxygen saturation, and the change in the volumetric pulse waveform of the blood in the limb or digit.

The foregoing summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 2:
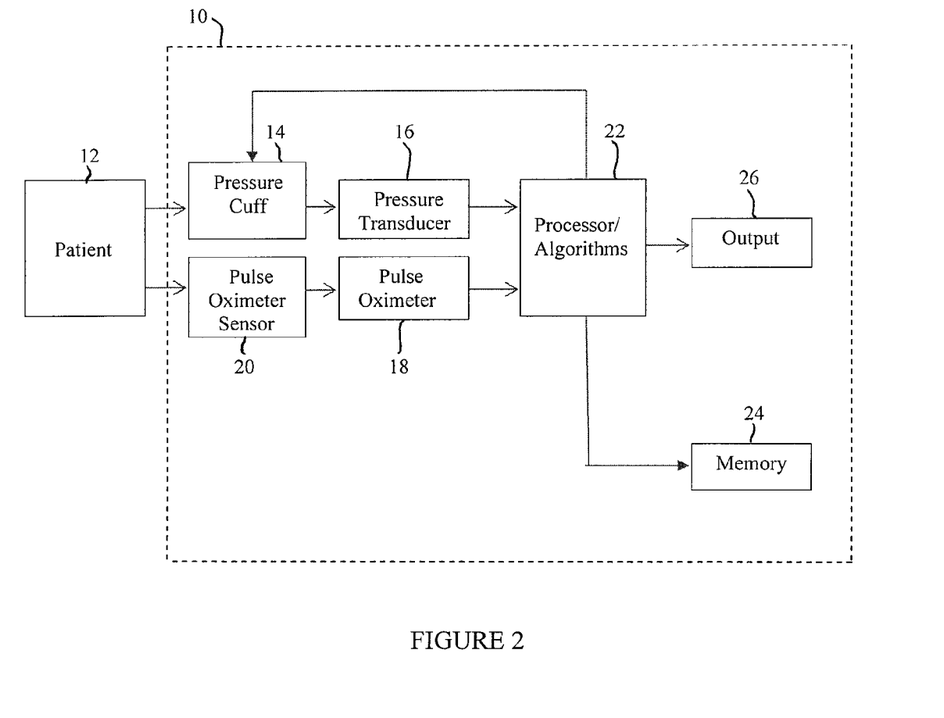
FIG. 2 is a general block diagram of an embodiment of an automated diagnostic apparatus configured in accordance with the present disclosure.

FIG. 2 illustrates a general block diagram of an automated medical diagnostic apparatus 10 configured to assess a peripheral vascular condition of a patient 12. In various embodiments, for example, the apparatus 10 uses automated algorithms to measure systolic blood pressure of the patient 12. The apparatus 10 may also determine indicators of peripheral vascular health, such as an ankle brachial index and/or a toe brachial index.

In at least one embodiment, the apparatus 10 includes an inflatable pressure cuff 14 that, in use, is fitted on a limb or a digit of a patient 12, who is the subject of testing. The pressure cuff 14 wraps around the limb or digit, and upon inflation and deflation, provides for stopping and allowing blood flow in the limb or digit depending on the pressure applied by the cuff.

A pressure transducer 16 directly connected to the pressure cuff 14 is configured to detect the mechanical pressure applied by the cuff to the limb or digit of the patient 12. The detected mechanical pressure is converted to electronic cuff pressure data inside the transducer. As described in further detail below, the pressure transducer 16 provides the electronic cuff pressure data to a processor 22.

The apparatus 10 is further configured to receive signals and/or data from a pulse oximeter 18 that includes a pulse oximeter sensor 20 placed on the patient 12. For example, the pulse oximeter sensor 20 is placed on a limb or digit of the patient 12. In various embodiments, the pulse oximeter sensor 20 is an optical device configured to transmit and receive light. The sensor 20 transmits optical signals through tissue of the patient 12 and converts received optical signals into electronic data. The sensor 20 provides the electronic data to the pulse oximeter 18 for processing, e.g., to calculate a perfusion index and/or other pulse oximeter data. Alternatively, the sensor 20 provides electronic signals to the pulse oximeter 18 and the pulse oximeter 18 converts the signals into electronic data. The pulse oximeter 18 may also be configured to control operational aspects of the pulse oximeter sensor 20 by issuing control signals to the sensor.

A clip sensor and a reflectance sensor are two common types of pulse oximeter sensor. A clip sensor clips onto a patient and transmits light through the tissue to a receiver on the opposite side of the tissue. Clip sensors are designed to be placed on digits (fingers or toes).

A reflectance sensor has both the transmit diodes and the receive photodiode on the same side of the tissue. The transmit diodes transmit light through the tissue and the photodiode receives light that is reflected back through the tissue. Reflectance sensors can be placed on a flat surface of the body such as the forehead or over the navicular bone of the foot (top of the foot over the arch).

Although both transmission- and reflectance-based pulse oximeter sensors exist, and suitable measurements can be performed using either type of sensor, for convenience of description, a transmission-based pulse oximeter sensor 20 is discussed herein in greater detail.

It should be noted that a pulse oximeter sensor differs from a Doppler transducer. For example, an optical source in the pulse oximeter sensor 20 transmits a wide beam of specific wavelengths of light into a volume or region of tissue, and a photodiode in the sensor 20 detects transmitted or reflected light at the specific wavelengths from that volume or region of tissue. A Doppler sensor or probe, on the other hand, transmits an ultrasound signal into a region of tissue, but because of its narrow beam, the Doppler instrument is used to measure blood velocity in specific vessels within that region. A pulse oximeter sensor 20 has some similarities to a PPG sensor, but a pulse oximeter sensor transmits and receives at least two different wavelengths of light, whereas a PPG sensor transmits and receives only a single wavelength.

Compared to a PPG, a pulse oximeter is the preferred choice for measuring peripheral vascular blood pressures because a pulse oximeter provides numeric data as well as waveform output. Such numeric data may include oxygen saturation ($SpO_2$) and perfusion index (PI) data, while the waveform output from a pulse oximeter may include those two parameters and a volumetric pulse waveform. Sophisticated digital signal processing may be used to generate the numeric data. A PPG, on the other hand, provides only a volumetric pulse waveform output, so evaluation of the output is typically performed visually, which is not nearly as accurate as a numeric evaluation. Moreover, the sensitivity of currently available pulse oximeters far exceeds that of PPG in terms of obtaining accurate data at low perfusion and in the presence of patient motion. Pulse oximetry parameters can be correlated with each other in terms of perfusion, oxygenation, and volumetric pulse waveform, which can be further used to validate a systolic pressure measurement as described herein. This type of correlation would not be possible with PPG alone.

Photoplethysmography (PPG) is almost exclusively found in vascular specialty centers where peripheral vascular testing is traditionally performed. PPG is not found in other areas of medicine. On the other hand, pulse oximetry is prolific in critical care areas of a hospital, but is not found in vascular centers. The knowledge and understanding of pulse oximetry technology (e.g., $SpO_2$ and PI) and its use in critical care, and of PPG technology and its application in vascular centers, are concentrated in their respective specialties and are not shared. It is unexpected and surprising to use $SpO_2$ and PI for vascular testing, as described herein, as application of such pulse oximetry parameters in vascular testing requires knowledge and understanding of both specialties.

Returning to FIG. 2, in various embodiments, the pulse oximeter 18 is configured to process the electronic data received from the sensor 20 and output pulse oximetry data to the processor 22. Such pulse oximetry data includes, but is not limited to, perfusion index (PI) data. In various embodiments, pulse oximetry data may also include a volumetric pulse waveform and/or oxygen saturation ($SpO_2$) data. In other embodiments, the pulse oximeter 18 may only provide $SpO_2$ and pulse rate data. Some pulse oximeters may or may not provide a volumetric pulse waveform or PI data to the processor 22. In such cases, PI data may potentially be determined by the processor 22 based on the signals or data received from the pulse oximeter 18. The processor 22 may also be configured to control operational aspects of the pulse oximeter 18 by issuing control signals to the pulse oximeter.

As mentioned above, in at least one embodiment, a pressure transducer 16 directly connected to the pressure cuff 14 converts raw measurements of cuff pressure to electronic pressure data that is automatically monitored by the processor 22. The pressure transducer 16 may provide such pressure data continuously or intermittently to the processor 22. The monitored pressure data is used by the processor 22 in determining the systolic blood pressure of the patient's limb or digit.

In at least one embodiment, the processor 22 is an electronic controller that implements computer-executable algorithms, typically stored in memory 24, and reads, processes, analyzes, calculates, and communicates data to an output 26. Memory 24 may comprise any form of a non-transitory computer-readable medium capable of storing computer-executable instructions that implement the algorithms described herein. In at least one embodiment, the processor 22 is responsible for controllably inflating the pressure cuff 14 to either a pre-set pressure or to a pressure determined in relation to the cessation of the patient's blood flow under the cuff 14.

In various embodiments, the processor 22 monitors the cuff pressure sensed by the pressure transducer 16 as well as data produced by the pulse oximeter 18 while inflating and deflating the pressure cuff 14. In other embodiments, the processor 22 monitors the cuff pressure and the pulse oximeter data during inflation or deflation only. As described herein, the processor 22 uses the pulse oximeter data (e.g., PI) to help identify systolic blood pressure events, and further uses the pressure data to determine the patient's systolic blood pressure.

A systolic blood pressure event occurs when the processor 22 determines that the patient's flow of blood under the pressure cuff 14 has either ceased or returned to flow. Systolic pressure represents systole or the point of peak contraction of the left ventricle of the heart. When the processor 22 determines that a systolic blood pressure event has occurred, the processor 22 captures the cuff pressure at that time and stores the cuff pressure in the memory 24. The stored cuff pressure may later be used, alone or in combination with other systolic pressure measurements, to assess the peripheral vascular condition of the patient 12. For example, the systolic pressure measurements may be used to compute an assessment index for the patient, such as an ABI and/or TBI. Alternatively or in addition, the cuff pressure data may be transferred to the output 26.

In various embodiments, several systolic pressure measurements are used to compute an ABI or TBI. While FIG. 2 illustrates only one pressure cuff 14, one transducer 16, one pulse oximeter 18, and one sensor 20, in other embodiments, the processor 22 may control and/or monitor two or more pressure cuffs and transducers, as well as control and/or monitor data received from two or more pulse oximeters, separately or simultaneously.

In some embodiments, the output 26 may be a data port to which various electronic devices may connect and receive data from the processor 22. In other embodiments, the output 26 may comprise one or more electronic devices that provide data in a human-perceptible form, e.g., a printer or a display screen. Such data may include (but are not limited to) systolic pressure determinations as well as assessment index data as discussed herein. In addition to delivering such data to the output 26, the processor 22 may also store such data in memory 24 for later retrieval.

Figure 3:
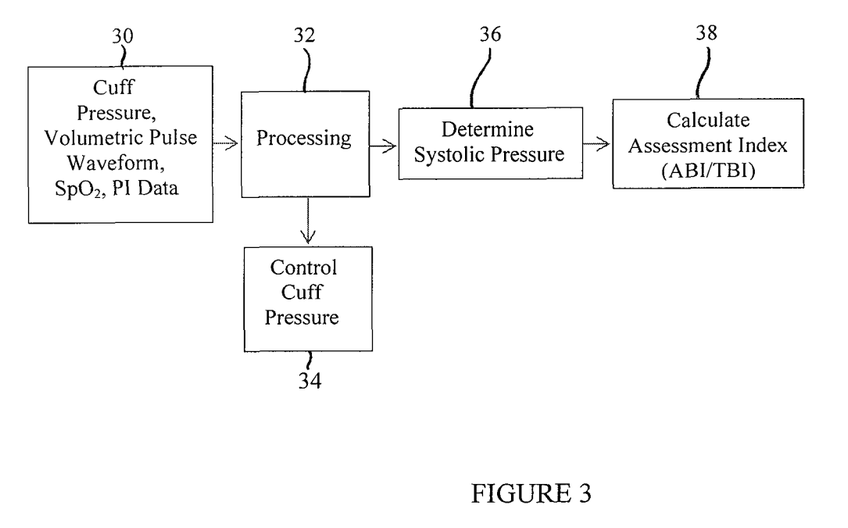
FIG. 3 is a general flow diagram of algorithms operating within an automated diagnostic apparatus as shown in FIG. 2.

FIG. 3 is a general flow diagram of algorithms and data that may be used by a medical device's diagnostic apparatus, such as apparatus 10 in FIG. 2, to assess a patient's peripheral vascular condition. As illustrated in FIG. 3, cuff pressure, volumetric pulse waveform, $SpO_2$, and PI data 30 are read simultaneously by the processor 22 in real-time from the pressure transducer(s) 16 and pulse oximeter(s) 18. Since all of the data is in electronic form, the processor 22 can receive this data via a variety of interfaces including (but not limited to) USB, RS232, and Serial Peripheral Interface, depending on the interface(s) available to the processor 22.

Data processing 32 as well as control of peripherals such as the pressure cuff 34 occurs in the processor 22, which is the central control point for the diagnostic apparatus 10. While the processor 22 monitors cuff pressure and pulse oximetry data, such as PI, volumetric pulse waveform, and $SpO_2$, the processor may simultaneously control the cuff pressure.

Cuff pressure is automatically controlled by one or more algorithms implemented in the processor 22. For example, a control algorithm 34 implemented by the processor 22 may determine that the pressure in the pressure cuff 14 needs to decrease. Accordingly, the processor 22 may issue a control signal to a pump attached to the cuff 14 (e.g., pump 16a in FIG. 4) that causes the pump to turn off. Another control signal would cause a valve connected to the cuff (e.g., valve 16b in FIG. 4) to open and allow air in the cuff to vent to the atmosphere at a controlled rate. If the control algorithm 34 determines that the pressure in the pressure cuff 14 needs to increase, control signals are issued that cause the valve to close and the pump to turn on, so as to inflate the cuff. Should the control algorithm 34 determine to maintain pressure in the pressure cuff as the next step, control signals are issued that enable the valve to remain closed and the pump to turn off. In various embodiments, the control algorithm 34 for controlling the cuff pressure is subject to control by data processing algorithms 32 executing in the processor 22, which controls the overall operation of the apparatus 10.

A patient's systolic blood pressure is determined by an algorithm 36 that monitors signals and/or data received from the pulse oximeter 18, such as PI, SpO$_2$, and volumetric pulse waveform, and the pressure applied by the cuff 14. Further detail regarding the processing that may be implemented by the algorithm 36 for determining systolic pressure is discussed later herein.

Regarding SpO$_2$, it is noted that pulse oximeter technology has been available and well understood for some time. Pulse oximeters have primarily been used to non-invasively measure the percentage of arterial hemoglobin saturated with oxygen (SpO$_2$). As local blood flow decreases, less oxygen is available to the tissue. When this occurs, SpO$_2$ decreases and there is a negative slope to the SpO$_2$ data output by the pulse oximeter 18. Related to this scenario, SpO$_2$ increases with increasing blood flow, and when this occurs, there is a positive slope to the SpO$_2$ data output by the pulse oximeter 18.

Perfusion index data indicates the variability of the patient's pulse as an index derived from the following classic pulse oximetry equation:

$$R \text{ (or Omega)} = (AC\text{red}/DC\text{red})/(AC\text{infrared}/DC\text{infrared}).$$

SpO$_2$ is determined as a function of R. The above fractions may be generated using data from the volumetric pulse waveform. The ACred parameter is the dynamic, pulsatile component of the patient's pulse as illuminated by using a red LED in the pulse oximeter sensor 20, and the DCred parameter is the non-pulsatile component due to blood exterior to the arterioles. The other LED typically used in a pulse oximeter sensor 20 emits an infrared wavelength. The ACinfrared parameter is the dynamic, pulsatile component of the patient's pulse as illuminated by using the infrared LED, and the DCinfrared parameter is the non-pulsatile component due to blood exterior to the arterioles. Generally, the SpO$_2$ value is primarily a function of R obtained from a calibration curve that may be generated in a laboratory environment for the pulse oximeter manufacturer.

The fraction in the denominator of R is considered to be the PI since oxygenated hemoglobin is more sensitive to infrared light than red light. As blood flow decreases, the infrared pulsatile component decreases, and thus the PI decreases and there is a negative slope to the PI data output by the pulse oximeter 18. Related to this scenario, PI increases with increasing blood flow, and in such circumstances, there is a positive slope to the PI data. PI thus reflects local changes in perfusion in the patient.

It is noted that the volumetric pulse waveform is a transduced representation of a patient's pulse. As blood flow in the patient decreases, the pulse amplitude decreases, and so as the volumetric pulse waveform decreases, there would be a negative slope to the volumetric pulse waveform data output by the pulse oximeter. Related to this scenario, volumetric pulse waveform increases with increasing blood flow, and in such circumstances, there is a positive slope to the volumetric pulse waveform data. The volumetric pulse waveform thus reflects local changes in perfusion in the patient.

As discussed earlier, an assessment of a patient's peripheral vascular condition may utilize a device, such as apparatus 10, having at least one pressure cuff 14 and at least one pulse oximeter 18. In many cases, the assessment involves two or more cuffs 14 and two or more pulse oximeters 18 being monitored simultaneously. Alternatively, an assessment with two or more cuffs and two or more pulse oximeters may be conducted serially. In either case, when a systolic blood pressure event occurs as determined by the processor 22, the algorithm 36 captures the cuff pressure at the time of the event, and possibly stores the pressure measurement in memory 24.

When the algorithm 36 has determined all required systolic pressure measurements, another algorithm 38 operating in the processor 22 may automatically calculate an assessment index, such as an ABI and/or TBI, using the systolic pressure measurements. Further details regarding the processing steps that may be implemented by the algorithm 38 for calculating an ABI and/or TBI are discussed below with regard to FIG. 5.

Figure 4:
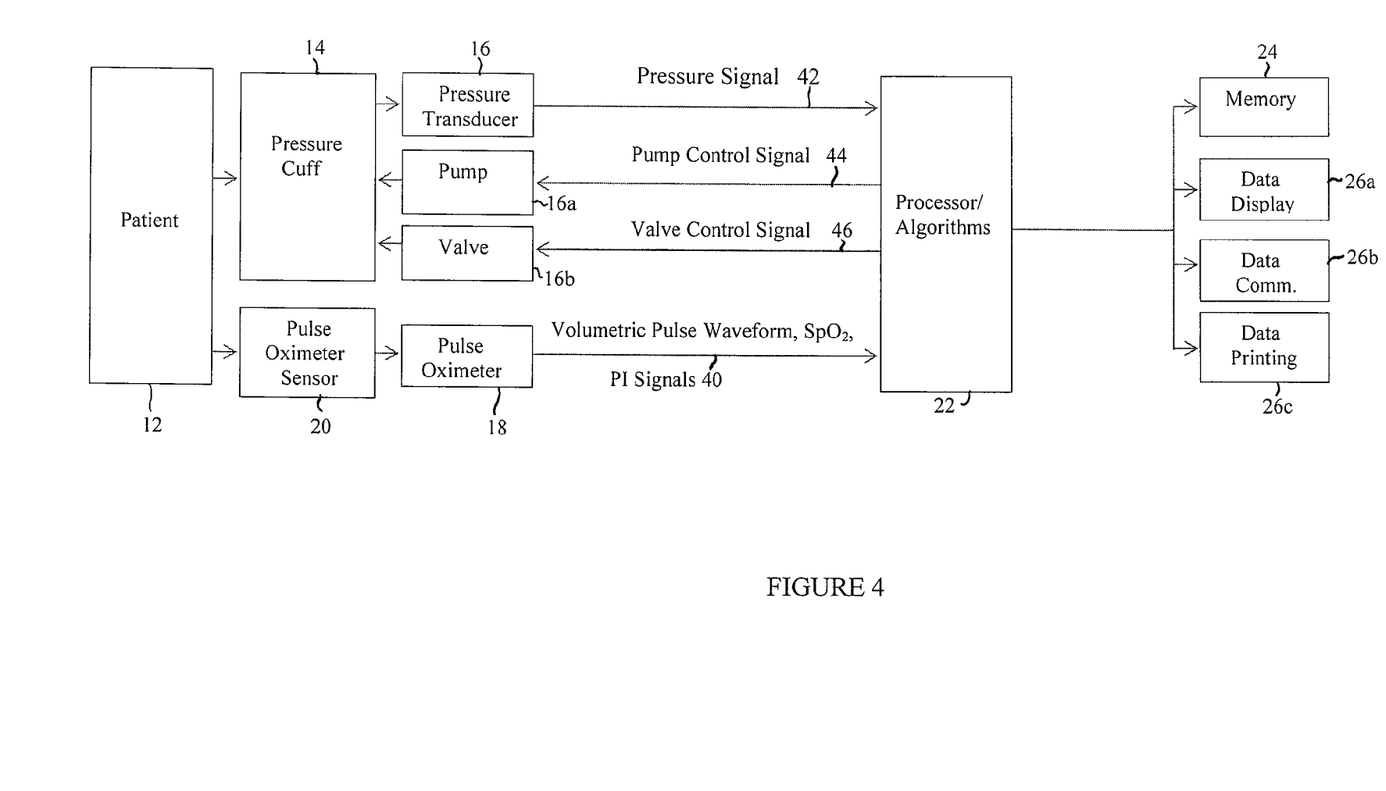
FIG. 4 is a detailed block diagram of the automated diagnostic apparatus.

FIG. 4 is a detailed block diagram of the apparatus 10 illustrated in FIG. 2. As indicated, a patient 12 is fitted with a pressure cuff 14 on a limb or digit. The pressure cuff 14 may be any one of a vascular or standard blood pressure cuff that is wrapped around the limb or digit to control blood flow in the limb or digit during a pressure measurement. A vascular cuff is typically constructed such that a bladder containing air completely surrounds the limb or digit. A vascular cuff is constructed so that the bladder is long enough to overlap when wrapped around the limb or digit in order to simultaneously compress all of the soft tissue under the cuff. Also, the cuff is constructed with proper width to avoid obtaining a pressure that is higher or lower than expected. When a systolic pressure event is detected as discussed below, and the patient's systolic pressure is determined, the pressure measurement represents the patient's systolic blood pressure at the site of the pressure cuff 14, not distal to the cuff site.

A pulse oximeter sensor 20 is placed on the limb or digit of the patient on the same side of the patient's body (left or right) as the cuff 14. The pulse oximeter sensor 20 uses at least two LEDs of different wavelengths to detect the volumetric pulse waveform in the patient's limb or digit. As mentioned earlier, there are two typical sensor designs for a pulse oximeter sensor. A transmission-based sensor transmits LED light through a limb or digit on one side, and uses a photodiode placed on the other side of the limb or digit to detect the transmitted light that passes through the limb or digit. A reflectance-based sensor has both the LEDs and a photodiode located on the same side of the limb or digit. Such a sensor transmits LED light into the tissue of the limb or digit, and detects light that has passed through the tissue and is reflected back to the sensor. In either case, signals representative of the light detected by the photodiode are provided to the pulse oximeter 18.

The pulse oximeter 18 monitors the signals provided by the sensor 20, processes the signals, and generates data, such as perfusion index (PI), volumetric pulse waveform, and oxygen saturation (SpO$_2$) for further evaluation. Processes for calculating and using PI data are known in the art. For example, European Patent Application No. 1861000 B1, titled "Method and device for determining the perfusion of blood in a body member" and incorporated by reference herein, discloses suitable processes that may be employed by the pulse oximeter 18. As another example, an article by Lima et al., published in Critical Care Medicine, 2002 June; 30(6):1210-3, titled "Use of a peripheral perfusion index derived from the pulse oximetry signal as a noninvasive indicator of perfusion" and incorporated by reference herein, also discloses processes for using PI.

Signals 40 from the pulse oximeter 18 are available to the processor 22 for further processing as described above. The data may be stored in a data store, such as memory 24. The data also may be output for display (e.g., using display device 26*a*), for communication to another device (e.g., using communication port 26*b*), or for printing (e.g., using printer 26*c*).

A pressure transducer 16 detects the pressure in the pressure cuff 14 and provides a pressure measurement signal 42 in a form that the processor 22 can read. The pressure signal provides the data necessary for the processor 22 to not only control the pressure in the pressure cuff 14, but also determine the patient's systolic pressure via one or more algorithms implemented by the processor 22. In various embodiments, the pressure transducer 16 is directly attached to the cuff 14.

The apparatus 10 includes a pump 16*a*, which is an electromechanical device that increases the pressure in the cuff 14 based on a pump control signal 44 received from the processor 22. The pump control signal 44 is determined by one or more algorithms operating in the processor 22. In various embodiments, the pump 16*a* is directly attached to the pressure cuff 14, and turns ON and OFF on demand under the control of the processor 22.

The apparatus 10 further includes a valve 16*b*, which is an electromechanical device that allows pressure in the pressure cuff to decrease based on a valve control signal 46 received from the processor 22. The valve control signal 46 is determined by one or more algorithms operating in the processor 22. In various embodiments, the valve 16*b* is directly attached to the pressure cuff 14, and opens and closes on demand under the control of the processor 22. When the valve 16*b* is opened, pressurized air within the cuff 14 is released to the atmosphere, thus allowing the cuff pressure to decrease.

In various embodiments, the pump control signal 44 may control the speed or volume of the air pumped into the cuff 14 to control the rate at which the cuff is inflated. Likewise, the valve control signal 46 may also control the degree to which or time that the valve 16*b* is opened, thus controlling the rate at which pressurized air within the cuff 14 is released. Through control of the pump 16*a* and the valve 16*b*, the processor 22 is able to controllably apply pressure via the cuff 14 to the limb or digit of the patient.

In various embodiments, the processor 22 may be an integrated circuit that operates according to computer-executable software instructions. The processor 22 is configured to read, process, analyze, interpret, and communicate data based on algorithms implemented by executing the software instructions. The processor 22 essentially comprises the intelligence of the apparatus 10 in the sense of command, control, analysis, and communication. It allows data to be processed, devices to be controlled simultaneously, and the process for assessing the vascular condition of the patient to be accomplished automatically.

In the illustrated embodiment, data obtained and processed by the processor 22 includes pressure data from the pressure transducer 16 and pulse oximeter data (e.g., PI, SpO$_2$, and volumetric pulse waveform) from the pulse oximeter 18. Based on this data, the processor 22 determines the patient's systolic pressure and calculates an assessment index, such as an ABI and/or TBI.

In various embodiments, data storage takes place inside an electrical storage device, such as memory 24, in which data may be temporarily or permanently stored for a desired amount of time. Examples of such a storage device may include but are not limited to non-volatile memory such as flash, or volatile memory such as RAM. The storage device may be fixed within the apparatus 10 or it may be removable from the apparatus 10.

Data display 26*a* occurs in the form of numerics and/or graphics generated on a screen as instructed by the processor 22. Typically, the subject matter displayed depends on the measurement parameter. Display screens may include, without limitation, standard computer monitors or touch LCD screens, and screens such as those found in smart phones, tablet computers, and other handheld wireless devices.

Data communications 26*b* are provided in accordance with a protocol by which data is transferred from the processor 22 or from data storage (e.g., memory 24) to another location. For example, and without limitation, DICOM, HL7, and other protocols may be used. Wired as well as wireless communication options are possible, as well as USB and Internet communications.

Data printing 26*c* may occur via a protocol by which data is sent to a printer. Wired as well as wireless printers operating over a wireless network are options.

Figure 5:
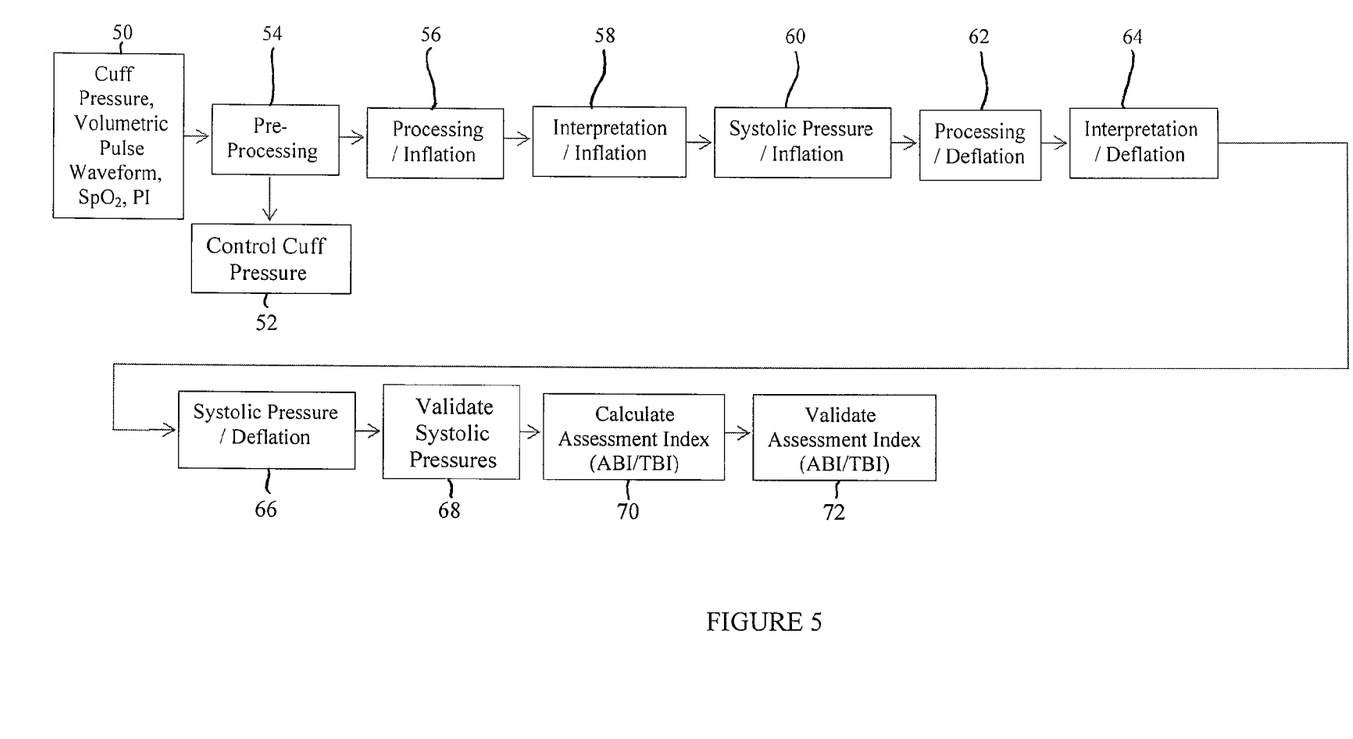
FIG. 5 is a detailed flow diagram of algorithms operating within the automated diagnostic apparatus.

FIG. 5 is a detailed flow diagram of algorithms that may be implemented by the diagnostic apparatus 10 described herein. As indicated, cuff pressure as well as PI, volumetric pulse waveform, and SpO$_2$ data from the pulse oximeter are read 50 by the processor. The data may be pre-processed 54 before or after receipt by the processor. For example, the data may be filtered to reject noise and spurious signals. Filtering may be performed in the time or frequency domains, but in either case, it is desirable that the filtering be fast and efficient to accommodate real-time diagnostic systems. The filtering performed 54 may occur throughout the measurement cycle.

In the illustrated embodiment, cuff pressure is automatically controlled 52 throughout the measurement cycle. Control of the cuff pressure is accomplished quickly so that the systolic pressure measurements correspond with the changes in PI, volumetric pulse waveform, and/or SpO$_2$ in the patient, and are thus indicative of a cessation of blood flow or a return of blood flow under the cuff.

After pre-processing, data are further processed 56 during inflation of the cuff in accordance with algorithms that monitor the cuff pressure and simultaneously detect changes in the pulse oximeter parameters, such as PI, volumetric pulse waveform, and SpO$_2$. For example, for each parameter, an algorithm interprets 58 the nature of change in the parameter and from that information, determines a systolic blood pressure 60 when a systolic pressure event has occurred (i.e., during inflation, when blood flow under the cuff has ceased). During inflation, PI, SpO$_2$, and volumetric pulse waveform data are expected to decrease, and when blood flow under the cuff has ceased, the data are expected to level out in that the rate of change is very small. In various embodiments, it is in the region of leveling that the instantaneous cuff pressure is captured and interpreted as the patient's systolic pressure. A decrease in PI values, for example, thus indicates the cessation of blood flow in the limb or digit to which the cuff is applied.

During deflation of the cuff, data are processed 62 in accordance with algorithms that monitor cuff pressure and simultaneously detect changes in the pulse oximeter parameters, such as PI, volumetric pulse waveform, and SpO$_2$. During deflation, the respective pulse oximeter parameters are expected to increase. For each parameter, an algorithm interprets 64 the nature of change in the parameter and from that information, determines a systolic blood pressure 66 when a systolic pressure event has occurred (i.e., when blood flow under the cuff has returned). In this scenario, it is in the region in which the parameter values turn upward that the instantaneous cuff pressure is captured and interpreted as the patient's systolic pressure. An increase in PI values, for example, thus indicates the return of blood flow in the limb or digit to which the cuff is applied.

After determining the patient's systolic blood pressure using one or more parameters of pulse oximeter data (e.g., PI, $SpO_2$, and/or volumetric pulse waveform), the pressure determination may be validated 68. By validating the pressure determination, the diagnostic apparatus 10 is better able to assure the clinician that the reported measurement meets specific criteria and is therefore reliable as a clinical measurement. In at least one embodiment, to be a valid clinical measurement, the determined systolic pressure should fall within a specific pressure range, as well as correlate with respect to $SpO_2$ and PI values obtained. This determination may be accomplished automatically at the end of each systolic pressure measurement. In some circumstances, the pressure measurement reported by apparatus 10 may be validated through correlation with data obtained using other devices, such as a Doppler instrument.

As mentioned earlier, the measurement process involves at least one cuff 14 and at least one pulse oximeter 18. Other configurations are possible. For example, depending on the configuration desired, it may be appropriate to measure six pressures, namely two brachial pressures, two dorsalis pedis pressures, and two posterior tibial pressures, automatically and simultaneously using two brachial and two ankle cuffs, with pulse oximeter sensors on relevant fingers and toes.

When the apparatus 10 has determined the systolic blood pressure measurements and the systolic blood pressure measurements have been validated, the apparatus may calculate 70 an assessment index for the patient, such as an ABI and/or TBI. The ABI may be determined as the highest of the ankle pressures on a given leg divided by the higher of the two brachial pressures. The TBI may be determined as the toe pressure divided by the highest of the brachial pressures. If the patient has two legs, he will have two ABI measurements calculated.

Once the ABI and/or TBI calculation has been performed, the assessment index may be validated 72 or correlated, e.g., in a manner as discussed earlier, with the $SpO_2$ and PI measurements or other measurement devices, to assure accuracy.

Informal testing has shown a good correlation between pulse oximeter-based systolic blood pressure measurements as described herein, and Doppler-based systolic blood pressure measurements. Doppler-based systolic blood pressure measurements of four subjects were obtained and compared with systolic blood pressure measurements obtained from observing oxygen saturation ($SpO_2$), perfusion index (PI), and volumetric pulse waveform data as displayed by a commercially available pulse oximeter. The commercially available pulse oximeter that was utilized is built and manufactured for medical device manufacturers to incorporate into their devices.

Results showed generally good correlation between Doppler-based and pulse oximeter-based systolic blood pressure measurements (within +/−5 mmHg) determined on inflation as well as deflation of the pressure cuff. The pulse oximeter is able to provide accurate pulse oximeter values at low perfusion and in the presence of patient motion.

As can be seen above, the algorithmic use of PI, $SpO_2$, and the volumetric pulse waveform allows for a more accurate determination of systolic blood pressure. The procedures discussed above also enable automatic determination of systolic blood pressures from potentially multiple pulse oximeters simultaneously, without using Doppler or PPG. Furthermore, numeric correlation of $SpO_2$, PI, and volumetric pulse waveform can be used to validate the resulting systolic pressure measurement.

While various representative embodiments, modes of operation, and principles of the invention have been described in the foregoing description, aspects of the invention that are protected by the following claims should not be construed as limited to the particular embodiments disclosed. The embodiments described herein are to be regarded as illustrative rather than restrictive. It will be appreciated that variations and changes may be made therein, and equivalents employed, without departing from the spirit of the present disclosure.

The embodiments of the invention in which an exclusive property or privilege is claimed are defined as follows:

1. An automated method of assessing a peripheral vascular condition of a patient, the method comprising, under the control of a computing device:
    applying pressure to a limb or digit of the patient sufficient to cease blood flow to the limb or digit distal to the applied pressure;
    using a pulse oximeter distal to the applied pressure to generate a plurality of pulse oximeter parameters relative to the limb or digit of the patient, wherein the plurality of pulse oximeter parameters comprises a perfusion index, oxygen saturation, and a volumetric pulse waveform;
    while increasing or decreasing the pressure applied to the limb or digit, determining a change in each of the plurality of pulse oximeter parameters indicative of a cessation of blood flow or a return of blood flow in the limb or digit;
    determining a systolic blood pressure in the limb or digit based on the pressure applied at the time of cessation of blood flow or the return of blood flow in the limb or digit as determined by the change in each of the pulse oximeter parameters; and
    assessing the peripheral vascular condition of the patient based on the systolic blood pressure determined in the limb or digit.

2. The method of claim 1, wherein applying pressure to the limb or digit of the patient comprises using a pressure cuff to compress the limb or digit.

3. The method of claim 2, wherein the pressure cuff inflates or deflates at a controlled rate.

4. The method of claim 1, wherein using a pulse oximeter to generate a plurality of pulse oximeter parameters comprises:
    transmitting light into the limb or digit;
    detecting light that was transmitted through tissue in the limb or digit; and
    calculating the plurality of pulse oximeter parameters relative to the limb or digit based on the light transmitted through the tissue.

5. The method of claim 1, wherein determining a change in the plurality of pulse oximeter parameters comprises identifying when a decrease in at least one of the plurality of pulse oximeter parameters occurs, in which the decrease is indicative of a cessation of blood flow in the limb or digit.

6. The method of claim 1, wherein determining a change in the plurality of pulse oximeter parameters comprises identifying when an increase in at least one of the plurality of pulse oximeter parameters occurs, in which the increase is indicative of a return of blood flow in the limb or digit.

7. The method of claim 1, further comprising calculating an assessment index for the patient by dividing a systolic blood pressure determined in an ankle of the patient by a systolic blood pressure determined in an arm of the patient.

8. The method of claim 1, further comprising calculating an assessment index for the patient by dividing a systolic blood pressure determined in a toe of the patient by a systolic blood pressure determined in an arm of the patient.

9. The method of claim 1, wherein assessing the peripheral vascular condition of the patient based on the systolic blood pressure determined in the limb or digit comprises using systolic blood pressure determined in both an ankle and a toe of the patient.

10. The method of claim 1, wherein using a pulse oximeter distal to the applied pressure to generate a plurality of pulse oximeter parameters relative to the limb or digit of the patient comprises simultaneously generating the plurality of pulse oximeter parameters relative to the limb or digit of the patient.

11. An apparatus for assessing a peripheral vascular condition of a patient, the apparatus comprising:
a pressure cuff configured to apply pressure to a limb or digit of the patient to cause cessation of blood flow in the limb or digit;
a pulse oximeter configured to generate a plurality of pulse oximeter parameters of the patient at a position on the limb or digit distal to the pressure cuff, wherein the plurality of pulse oximeter parameters comprises a perfusion index, oxygen saturation, and a volumetric pulse waveform; and
a processor configured to:
cause the pressure cuff to controllably apply or release a pressure to the limb or digit of the patient sufficient to cease blood flow to the limb or digit distal to the pressure cuff,
monitor the plurality of pulse oximeter parameters generated by the pulse oximeter relative to the limb or digit and determine a change in each of the plurality of pulse oximeter parameters indicative of a cessation of blood flow or a return of blood flow in the limb or digit, and
determine a systolic blood pressure in the limb or digit based on the pressure applied by the pressure cuff when the cessation of blood flow or the return of blood flow occurred as determined by the change in each of the plurality of pulse oximeter parameters.

12. The apparatus of claim 11, wherein the pressure cuff is configured to apply pressure to the limb or digit by inflating and thereby compressing the limb or digit, and wherein the processor is configured to cause the pressure cuff to controllably apply or release a pressure by inflating or deflating the pressure cuff at a controlled rate.

13. The apparatus of claim 11, further comprising one or more optical devices configured to transmit and detect light when attached to the patient, wherein the plurality of pulse oximeter parameters are generated by the pulse oximeter using the one or more optical devices.

14. The apparatus of claim 13, wherein the pulse oximeter is configured to transmit light into or onto the limb or digit and detect light transmitted through or reflected from tissue in the limb or digit, and wherein the processor is configured to monitor the plurality of pulse oximeter parameters by the pulse oximeter based on the light transmitted through or reflected from the tissue.

15. The apparatus of claim 14, wherein the pulse oximeter comprises an optical source configured to transmit light at specific wavelengths and a photodiode configured to detect light transmitted at the specific wavelengths.

16. The apparatus of claim 11, wherein the processor is further configured to calculate an assessment index for the patient by dividing a systolic blood pressure determined in an ankle of the patient by a systolic blood pressure determined in an arm of the patient.

17. The apparatus of claim 11, wherein the processor is further configured to calculate an assessment index for the patient by dividing a systolic blood pressure determined in a toe of the patient by a systolic blood pressure determined in an arm of the patient.

18. The apparatus of claim 11, wherein the pulse oximeter is configured to simultaneously generate the plurality of pulse oximeter parameters of the patient at a position on the limb or digit distal to the pressure cuff.

19. An automated method of assessing a peripheral vascular condition of a patient, the method comprising, under the control of a computing device:
applying pressure to a limb or digit of the patient;
using a pulse oximeter to generate a plurality of pulse oximeter parameters relative to the limb or digit of the patient, wherein the plurality of pulse oximeter parameters comprises a perfusion index, oxygen saturation, and a volumetric pulse waveform;
while increasing or decreasing the pressure applied to the limb or digit, determining a change in each of the plurality of pulse oximeter parameters indicative of a change in blood flow in the limb or digit;
determining a systolic blood pressure in the limb or digit based on the pressure applied at the time of change in blood flow in the limb or digit as determined by the change in each of the plurality of pulse oximeter parameters; and
assessing the peripheral vascular condition of the patient based on the systolic blood pressure determined and pulse oximeter parameter changes in the limb or digit.

* * * * *